(12) United States Patent
Nishimura et al.

(10) Patent No.: US 8,039,633 B2
(45) Date of Patent: Oct. 18, 2011

(54) METHOD FOR PRODUCING NICOTINIC ACID DERIVATIVE OR SALT THEREOF

(75) Inventors: Shigeyuki Nishimura, Kusatsu (JP); Fumio Kanamori, Kusatsu (JP); Masashi Hisamoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 882 days.

(21) Appl. No.: 11/911,725

(22) PCT Filed: Apr. 20, 2006

(86) PCT No.: PCT/JP2006/308318
§ 371 (c)(1),
(2), (4) Date: Oct. 17, 2007

(87) PCT Pub. No.: WO2006/115171
PCT Pub. Date: Nov. 2, 2006

(65) Prior Publication Data
US 2009/0054656 A1 Feb. 26, 2009

(30) Foreign Application Priority Data
Apr. 21, 2005 (JP) .................................. 2005-123899

(51) Int. Cl.
*C07D 211/78* (2006.01)
*C07D 211/72* (2006.01)
(52) U.S. Cl. ........................................ 546/327; 546/290
(58) Field of Classification Search ................... 546/290, 546/327
See application file for complete search history.

(56) References Cited

U.S. PATENT DOCUMENTS

| 3,879,403 A | * | 4/1975 | Kuhla et al. | 546/292 |
| 4,980,357 A | * | 12/1990 | Goldstein et al. | 514/278 |

FOREIGN PATENT DOCUMENTS

| EP | 0 494770 | 1/1992 |
| JP | 50-13379 | 2/1975 |
| JP | 64-71882 | 3/1989 |
| JP | 6-41116 | 2/1994 |

OTHER PUBLICATIONS

Okada et al., Org. Biomol. Chem, 2003, vol. 1, pp. 2506-2511.*
Sarges, Reinhard et al., "Spiro Hydantoin Aldose Reductase Inhibitors Derived from 8-Aza-4-chromanones", Journal of Medicinal Chemistry, vol. 33, No. 7, pp. 1859 to 1865, 1990.
Hirokawa, Yoshimi et al., "An Efficient Synthesis of 5-Bromo-2-methoxy-6-methylaminopyridine-3- carboxylic Acid, Chemical & Pharmaceutical Bulletin", vol. 48, No. 12, pp. 1847 to 1853, 2000.
Hirokawa, Yoshimi et al., "Synthesis and Structure-Affinity Relationships of Novel N- (1-Ethyl-4-methylhexahydro-1, 4-diazepin-6-yl) pyridine-3-carboxamides with Potent Serotonin 5-$HT_3$ and Dopamine $D_2$ Receptor Antagonistic Activity", Journal of Medicinal Chemistry, vol. 46, No. 5, pp. 702 to 715, 2003.

* cited by examiner

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

To provide a method for producing a specific nicotinic acid derivative or a salt thereof. A method for producing a nicotinic acid derivative represented by the formula (I):

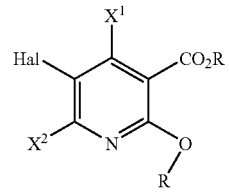

wherein each of $X^1$ and $X^2$ which are independent of each other, is a hydrogen atom, a halogen atom, an alkyl group, an alkoxy group, a haloalkyl group or a haloalkoxy group; R is an alkyl group; and Hal is a chlorine atom or a bromine atom; or a salt thereof, is provided which comprises reacting a compound represented by the formula (II):

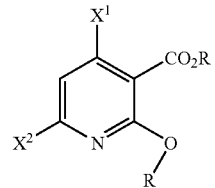

is wherein $X^1$, $X^2$ and R are as defined above, or a salt thereof, with a halogenating agent.

16 Claims, No Drawings

METHOD FOR PRODUCING NICOTINIC ACID DERIVATIVE OR SALT THEREOF

TECHNICAL FIELD

The present invention relates to a method for producing a nicotinic acid derivative or a salt thereof, which is useful as an intermediate for pharmaceuticals or agricultural chemicals.

BACKGROUND ART

Some of nicotinic acid derivatives represented by the after-mentioned formula (I) and compounds represented by the after-mentioned formula (II) as starting materials for the production thereof, are included in the compounds represented by the formula (I) disclosed in EP-494770A. However, in such publication, there is no specific disclosure of the respective compounds or a method for their production. On the other hand, some of compounds represented by the after-mentioned formula (III) are disclosed as compounds of the formula (VI) in JP-A-6-41116 at pages 41 and 58 to 69.

Patent Document 1: EP-494770A
Patent Document 2: JP-A-6-41116

DISCLOSURE OF THE INVENTION

Problem to be Solved by the Invention

Heretofore, various methods for producing nicotinic acid derivatives have been known, but they are not necessarily efficient for producing nicotinic acid derivatives having specific substituent patterns. Further, a method for efficiently producing a nicotinic acid derivative represented by the after-mentioned formula (I) or a salt thereof has been desired.

Means to Solve the Problem

The present inventors have conducted a study to solve the above problem and as a result, have found a method for producing a nicotinic acid derivative represented by the after-mentioned formula (I) or a salt thereof, wherein a compound represented by the after-mentioned formula (III) or a salt thereof is used as a starting material, and have accomplished the present invention.

Namely, the present invention provides a method for producing a nicotinic acid derivative represented by the formula (I):

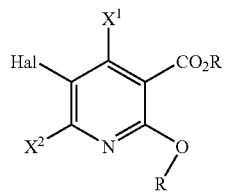

wherein each of $X^1$ and $X^2$ which are independent of each other, is a hydrogen atom, a halogen atom, an alkyl group, an alkoxy group, a haloalkyl group or a haloalkoxy group; R is an alkyl group; and Hal is a chlorine atom or a bromine atom; or a salt thereof, which comprises reacting a compound represented by the formula (II):

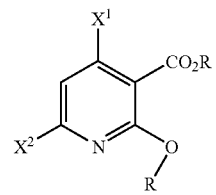

wherein $X^1$, $X^2$ and R are as defined above, or a salt thereof, with a halogenating agent.

Further, the present invention provides the method for producing the nicotinic acid derivative of the above formula (I) or a salt thereof, which comprises (i) a first step of reacting a compound represented by the formula (III):

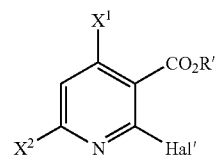

wherein each of $X^1$ and $X^2$ which are independent of each other, is a hydrogen atom, a halogen atom, an alkyl group, an alkoxy group, a haloalkyl group or a haloalkoxy group; R' is an alkyl group; and Hal' is a fluorine atom, a chlorine atom or a bromine atom; or a salt thereof, with an alkali metal alkoxide represented by the formula (IV):

RO-M wherein R is an alkyl group, and M is an alkali metal atom, to obtain a compound represented by the formula (II):

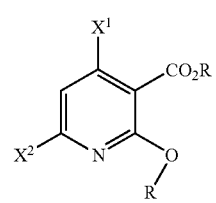

wherein $X^1$, $X^2$ and R are as defined above, or a salt thereof, and (ii) a second step of reacting the compound of the formula (II) or a salt thereof obtained in the first step, with the halogenating agent, to obtain a nicotinic acid derivative represented by the formula (I):

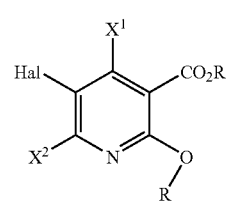

wherein $X^1$, $X^2$ and R are as defined above, and Hal is a chlorine atom or a bromine atom, or a salt thereof.

Further, the present invention provides a method for producing a nicotinic acid represented by the formula (V):

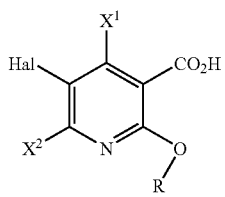

wherein $X^1$, $X^2$, R and Hal are as defined below, or a salt thereof, which comprises hydrolyzing a nicotinic acid derivative represented by the formula (I)

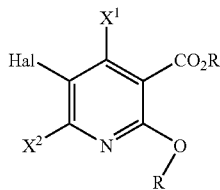

wherein each of $X^1$ and $X^2$ which are independent of each other, is a hydrogen atom, a halogen atom, an alkyl group, an alkoxy group, a haloalkyl group or a haloalkoxy group; R is an alkyl group; and Hal is a chlorine atom or a bromine atom; or a salt thereof.

The halogen atom, or the halogen moiety in the haloalkyl group or the haloalkoxy group, represented by $X^1$ or $X^2$ in the formula (I), (II), (III) or (V) may be fluorine, chlorine, bromine or iodine, preferably fluorine, chlorine or bromine.

The alkyl moiety contained in the formula (I), (II), (III) or (V) may, for example, be a $C_{1-6}$ alkyl (such as methyl, ethyl, propyl, isopropyl, butyl, isobutyl or t-butyl).

The alkoxy moiety contained in the formula (I), (II), (III) or (V) may, for example, be a $C_{1-6}$ alkoxy (such as methoxy, ethoxy, propoxy, isopropoxy, butoxy, isobutoxy or t-butoxy).

The compound of the formula (I), (II), (III) or (V) may form a salt together with an acidic substance and may, for example, form an inorganic salt such as a hydrochloride, a hydrobromide, a phosphate, a sulfate or a nitrate; or an organic salt such as an acetate, a p-toluenesulfonate, a methanesulfonate or a propanesulfonate. Further, the compound of the formula (V) may form an alkali metal salt or an alkaline earth metal salt and may, for example, form a sodium salt, a potassium salt, a magnesium salt or a calcium salt.

EFFECTS OF THE INVENTION

According to the present invention, it becomes possible to efficiently produce a nicotinic acid derivative or its salt useful as an intermediate for pharmaceuticals or agricultural chemicals.

BEST MODE FOR CARRYING OUT THE INVENTION

Now, the method for producing a nicotinic acid derivative or its salt of the present invention will be described in detail with reference to the reaction flow. The nicotinic acid derivative of the formula (I) or its salt is produced by reacting a compound of the formula (II) or its salt with a halogenating agent containing a chlorine atom or a bromine atom. However, it is efficient to produce it by two step reactions shown by the following flow.

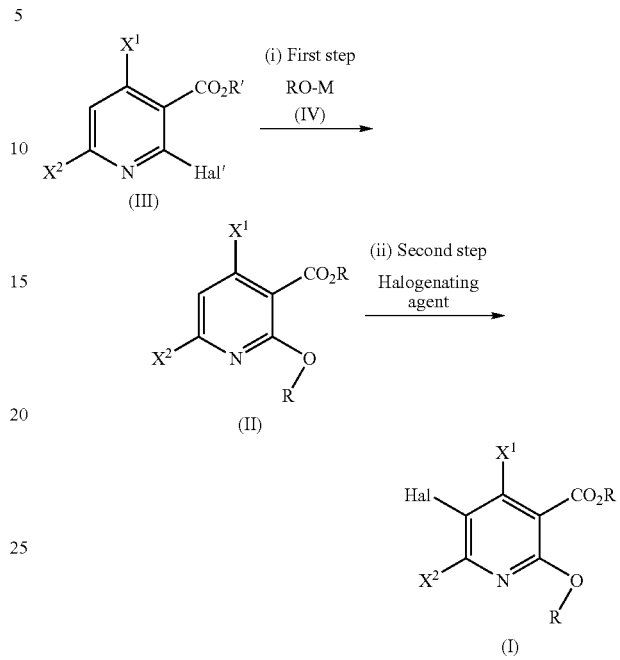

In the above formulae, $X^1$, $X^2$, Hal, Hal', R, R' and M are as defined above.

The reaction of the first step of reacting a compound of the formula (III) or its salt with an alkali metal alkoxide represented by the formula (IV) to produce a compound of the above formula (II) or its salt, is preferably carried out in the presence of a solvent at a reaction temperature of from 0 to 150° C. for a reaction time of from 0.1 to 24 hours. Here, the alkyl group represented by R' in the compound of the formula (III) and the alkyl group represented by R in the alkali metal alkoxide represented by the formula (IV) may be the same or different. This reaction may be carried out also under reduced pressure.

The alkali metal alkoxide of the formula (IV) to be used for the reaction of the first step may, for example, be sodium methoxide, sodium ethoxide or potassium methoxide. Among them, it is preferred to use sodium methoxide. The alkali metal alkoxide is preferably used in an amount of from 1.0 to 5.0 mols per mol of the compound of the formula (III) or its salt.

The solvent to be used for the reaction of the first step is not particularly limited so long as it will not be involved in the reaction. For example, an aromatic hydrocarbon such as benzene, toluene or xylene, an aliphatic hydrocarbon such as hexane or cyclohexane, a halogenated hydrocarbon such as methylene chloride or 1,2-dichloroethane, an alcohol such as methanol or ethanol, an ether such as tetrahydrofuran or 1,2-dimethoxyethane, or an aprotic polar solvent such as N,N-dimethylformamide or dimethylsulfoxide may be mentioned. Among them, it is preferred to use an alcohol.

The reaction of the second step of reacting the compound of the formula (II) or its salt with a halogenating agent containing a chlorine atom or a bromine atom to produce a nicotinic acid derivative of the above formula (I) or its salt, is preferably carried out in the presence of a base or a solvent at a reaction temperature of from 0 to 150° C. for a reaction time of from 0.1 to 24 hours. This reaction may be carried out under reduced pressure.

The halogenating agent containing a chlorine atom or a bromine atom to be used for the reaction of the second step is not particularly limited so long as it is useful for usual chlorination or bromination. For example, chlorine, bromine, sulfuryl chloride, sodium hypochlorite, N-chlorosuccinimide, N-bromosuccinimide, 1,3-dichloro-5,5-dimethylhydantoin or 1,3-dibromo-5,5-dimethylhydantoin may be mentioned. Among them, it is preferred to use chlorine or bromine. Such a halogenating agent is preferably used in an amount of from 1.0 to 5.0 mols per mol of the compound of the formula (II).

A base to be used for the reaction of the second step may, for example, be an alkali metal hydroxide such as sodium hydroxide or potassium hydroxide; an alkali metal carbonate such as sodium carbonate or potassium carbonate; an alkali metal acetate such as sodium acetate or potassium acetate; an alkali metal hydrogencarbonate such as sodium hydrogencarbonate or potassium hydrogencarbonate; or an amine such as pyridine or triethylamine. Among them, it is preferred to use sodium acetate. Such a base is preferably used in an amount of from 0.1 to 5.0 mols per mol of the compound of the formula (II).

The solvent to be used for the reaction of the second step is not particularly limited so long as it will not be involved in the reaction. For example, aromatic hydrocarbon such as chlorobenzene or dichlorobenzene; an aliphatic hydrocarbon such as hexane or cyclohexane; a halogenated hydrocarbon such as methylene chloride or 1,2-dichloroethane; an ether such as tetrahydrofuran or 1,2-dimethoxyethane; a carboxylic acid such as acetic acid; an ester such as methyl acetate or ethyl acetate; a nitrile such as acetonitrile or propionitrile; or an aprotic polar solvent such as N,N-dimethylformamide or dimethylsulfoxide may be mentioned. Among them, it is preferred to use an ester.

A reaction for hydrolyzing the above-mentioned compound of the formula (I) or its salt to produce a compound of the formula (V) or its salt is preferably carried out in water or in a solvent containing water at a reaction temperature of from 0 to 150° C. for a reaction time of from 0.1 to 24 hours. This reaction may be carried out under reduced pressure.

The base to be used for the hydrolysis may, for example, be an alkali metal hydroxide such as sodium hydroxide or potassium hydroxide; an alkaline earth metal hydroxide such as magnesium hydroxide or calcium hydroxide; an alkali metal carbonate such as sodium carbonate or potassium carbonate; an alkaline earth metal carbonate such as magnesium carbonate or calcium carbonate; or an alkali metal hydrogencarbonate such as sodium hydrogencarbonate or potassium hydrogencarbonate. Among them, it is preferred to use sodium hydroxide. The base is preferably used in an amount of at least one mol per mol of the compound of the formula (I) or its salt.

The solvent to be used for the hydrolysis is not particularly limited so long as it will not be involved in the reaction. For example, an aromatic hydrocarbon such as benzene, toluene or xylene; an aliphatic hydrocarbon such as hexane or cyclohexane; a halogenated hydrocarbon such as methylene chloride or 1,2-dichloroethane; an alcohol such as methanol or ethanol; an ether such as tetrahydrofuran or 1,2-dimethoxyethane; a nitrile such as acetonitrile or propionitrile; or an aprotic polar solvent such as N,N-dimethylformamide or dimethylsulfoxide may be mentioned. However, the hydrolysis is preferably carried out in water or in an alcohol containing water.

After completion of the hydrolysis, the compound of the formula (V) is treated for neutralization with a mineral acid such as hydrochloric acid or sulfuric acid to form an alkali metal salt or an alkaline earth metal salt, whereby a compound of the formula (V) will be obtained. Otherwise, without such neutralization treatment, an alkali metal salt or an alkaline earth metal salt of the compound of the formula (V) may be isolated.

The above method for producing the compound of the formula (V) or its salt may optionally be combined with the above-mentioned method for producing the nicotinic acid derivative of the formula (I) or its salt. Such embodiments will be described below.

(1) A method which comprises reacting a compound represented by the formula (II):

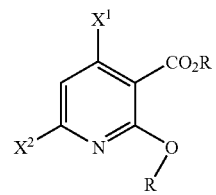

wherein $X^1$, $X^2$ and R are as defined above, or a salt thereof, with a halogenating agent to obtain a nicotinic acid derivative represented by the formula (I):

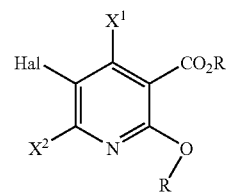

wherein $X^1$, $X^2$ and R are as defined above, and Hal is a chlorine atom or a bromine atom, or a salt thereof, and hydrolyzing it to obtain a nicotinic acid represented by the formula (V):

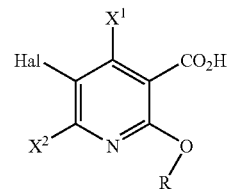

wherein $X^1$, $X^2$, R and Hal are as defined above, or a salt thereof.

(2) A method for producing a nicotinic acid represented by the above formula (V) or its salt, which comprises (i) a first step of reacting a compound represented by the formula (III):

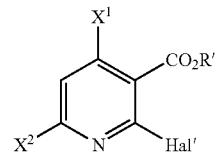

wherein each of $X^1$ and $X^2$ which are independent of each other, is a hydrogen atom, a halogen atom, an alkyl group, an alkoxy group, a haloalkyl group or a haloalkoxy group; R' is an alkyl group; and Hal' is a fluorine atom, a chlorine atom or a bromine atom; or a salt thereof, with an alkali metal alkoxide represented by the formula (IV):

RO-M wherein R is an alkyl group, and M is an alkali metal atom, to obtain a compound represented by the formula (II):

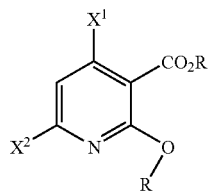

wherein $X^1$, $X^2$ and R are as defined above, or a salt thereof, (ii) a second step of reacting the compound of the formula (II) or a salt thereof obtained in the first step, with the halogenating agent, to obtain a nicotinic acid derivative represented by the formula (I):

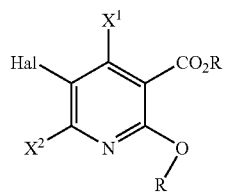

wherein $X^1$, $X^2$ and R are as defined above, and Hal is a chlorine atom or a bromine atom, or a salt thereof, and (iii) a third step of hydrolyzing the compound of the formula (I) or a salt thereof obtained in the second step, to obtain a nicotinic acid represented by the formula (V):

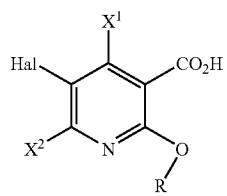

wherein $X^1$, $X^2$, R and Hal are as defined above, or a salt thereof.

(3) The method according to (1) or (2), wherein the compound of the formula (I) is methyl 5-chloro-2-methoxy-4-methyl nicotinate, the compound of the formula (II) is methyl 2-methoxy-4-methyl nicotinate, and the compound of the formula (V) is 5-chloro-2-methoxy-4-methyl nicotinic acid.

(4) The method according to (2), wherein the compound of the formula (III) is ethyl 2-chloro-4-methyl nicotinate or methyl 2-chloro-4-methyl nicotinate.

EXAMPLES

Now, the present invention will be described with reference to Examples, but it should be understood that the present invention is by no means restricted to such Examples.

Preparation Example 1

Into a 300 ml four necked flask equipped with a stirrer, a condenser and a thermometer, 137.8 g (714 mmol) of 28% sodium methylate methanol solution was charged, and while the internal temperature was maintained at 50° C., 48 ml of a methanol solution containing 47.5 g (238 mmol) of ethyl 2-chloro-4-methyl nicotinate was dropwise added, followed by stirring for 1 hour. The reaction solution was put into 500 ml of water and extracted with diethyl ether, followed by distillation under reduced pressure to obtain 27 g (yield: 63%) of methyl 2-methoxy-4-methyl nicotinate (boiling point: 95° C./7 mmHg).

Preparation Example 2

Into a 500 ml four necked flask equipped with a stirrer, a thermometer, a condenser and an $N_2$ gas supply tube, 203 g (1.05 mol) of a 28% sodium methylate methanol solution was charged in an $N_2$ atmosphere. While the internal temperature was maintained at not higher than 40° C., 92.8 g (0.5 mol) of methyl 2-chloro-4-methyl nicotinate was dropwise added over a period of about 30 minutes. After completion of the dropwise addition, while the internal temperature was maintained from 45 to 50° C., the reaction was carried out for about 4 hours till disappearance of the starting materials. After completion of the reaction, about 100 ml of methanol in the system was distilled off under reduced pressure, and then the reaction solution was put into a mixed solution of 390 g of a 7% sulfuric acid aqueous solution and 300 ml of toluene with stirring. After extraction and liquid separation, the toluene layer was washed with 150 ml of a 0.5% sodium hydrogencarbonate aqueous solution. After distilling off toluene, a fraction of from 85 to 92° C./5 mmHg i.e. 83.3 g (yield: 92%) of methyl 2-methoxy-4-methyl nicotinate was obtained by distillation under reduced pressure.

Preparation Example 3

Into a 500 ml four necked flask quipped with a stirrer, a thermometer, a condenser and a $Cl_2$ gas supply tube, 90.6 g (0.5 mol) of methyl 2-methoxy-4-methyl nicotinate, 300 ml of ethyl acetate and 49.2 g (0.6 mol) of sodium acetate were charged. While the internal temperature was maintained at 70° C., chlorine gas (supply rate: 10 g/hr) was introduced for about 4 hours, and upon confirming disappearance of the starting materials, the reaction was terminated. The reaction mixture was put into 700 ml of cool water, and 200 ml of ethyl acetate was added, followed by extraction and liquid separation. Then, the ethyl acetate layer was washed with 150 ml of a 1% sodium hydrogencarbonate aqueous solution, and dried over anhydrous sodium sulfate, whereupon ethyl acetate was distilled off to obtain 105.6 g (crude yield: 98%) of crude crystals of desired methyl 5-chloro-2-methoxy-4-methyl nicotinate. This product was recrystallized from methanol to obtain 91.8 g (melting point: 43-44° C.) of a recrystallized product.

Preparation Example 4

Into a 1,000 ml four necked flask equipped with a stirrer, a condenser and a thermometer, 107.8 g (0.5 mol) of methyl 5-chloro-2-methoxy-4-methyl nicotinate and 210 g (0.525 mol) of a 10% sodium hydroxide aqueous solution were charged, followed by stirring for 2 hours at an internal temperature of 90° C. The reaction solution was left to cool and then a 15% sulfuric acid aqueous solution was dropwise added for neutralization and crystallization. Precipitated crystals were collected by filtration and then dried to obtain 99.3 g (yield: 98%) of 5-chloro-2-methoxy-4-methyl nicotinic acid (melting point: 127-129° C.).

INDUSTRIAL APPLICABILITY

The method of the present invention is useful as an efficient method for producing a nicotinic acid derivative or its salt which is useful as an intermediate for pharmaceuticals or agricultural chemicals.

The entire disclosure of Japanese Patent Application No. 2005-123899 filed on Apr. 21, 2005 including specification, claims, drawings and summary is incorporated herein by reference in its entirety.

The invention claimed is:

1. A method for producing a nicotinic acid derivative represented by formula (I):

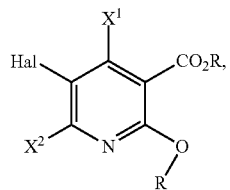

(I)

wherein:
each of $X^1$ and $X^2$ which are independent of each other, is a hydrogen atom, a halogen atom, an alkyl group, an alkoxy group, a haloalkyl group, or a haloalkoxy group;
R is an alkyl group; and
Hal is a chlorine atom or a bromine atom, or a salt of the compound represented by formula (I),
the method comprising:
reacting a compound represented by formula (II):

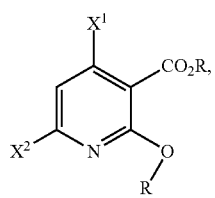

(II)

or a salt of the compound represented by formula (II), with a halogenating agent.

2. The method for producing a nicotinic acid derivative or a salt thereof according to claim 1, the method comprising:
(i) reacting a compound represented by formula (III):

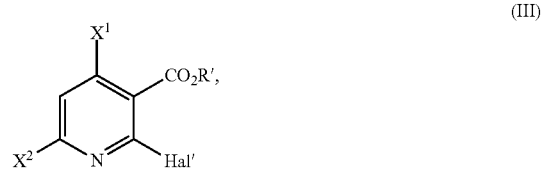

(III)

wherein:
each of $X^1$ and $X^2$ which are independent of each other, is a hydrogen atom, a halogen atom, an alkyl group, an alkoxy group, a haloalkyl group, or a haloalkoxy group;
R' is an alkyl group; and
Hal' is a fluorine atom, a chlorine atom, or a bromine atom, or
a salt of the compound represented by formula (III), with an alkali metal alkoxide represented by formula (IV):

RO-M       (IV), wherein R is an alkyl group, and M is an alkali metal atom, to obtain the compound represented by formula (II):

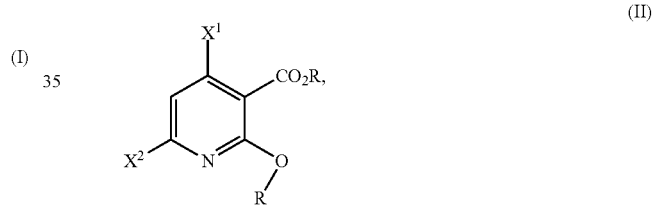

(II)

or a salt of the compound represented by formula (II), and
(ii) reacting the compound of formula (II), or the salt of the compound represented by formula (II), obtained in the reacting (i),
with the halogenating agent, to obtain the nicotinic acid derivative represented by formula (I):

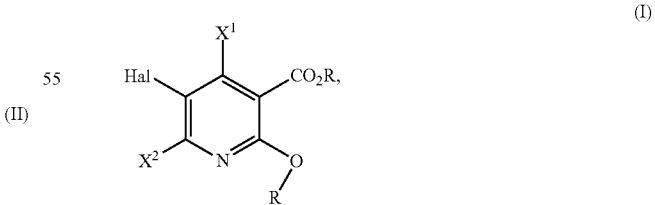

(I)

or the salt of the compound represented by formula (I).

3. The method according to claim 2, wherein the alkali metal alkoxide of formula (IV) is an alkali metal methoxide.

4. The method according to claim 1, wherein the halogenating agent is chlorine or bromine.

5. A method for producing a nicotinic acid represented by formula (V):

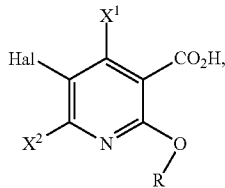

(V)

wherein $X^1$, $X^2$, R and Hal are as defined below, or a salt of the compound represented by formula (V), the method comprising:
hydrolyzing a nicotinic acid derivative represented by formula (I):

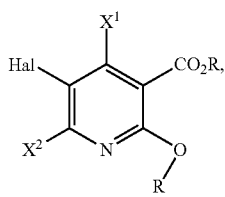

(I)

wherein:
each of $X^1$ and $X^2$ which are independent of each other, is a hydrogen atom, a halogen atom, an alkyl group, an alkoxy group, a haloalkyl group, or a haloalkoxy group;
R is an alkyl group; and
Hal is a chlorine atom or a bromine atom, or a salt of the compound represented by formula (I).

6. The method according to claim 5, which comprises
(i) reacting a compound represented by formula (II):

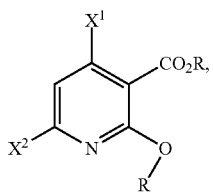

(II)

or a salt of the compound represented by formula (II),
with a halogenating agent to obtain the nicotinic acid derivative represented by formula (I):

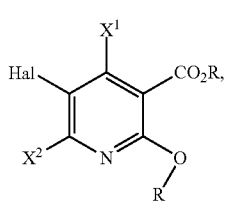

(I)

wherein Hal is a chlorine atom or a bromine atom, or the salt of the compound represented by formula (I), and
(ii) hydrolyzing the compound represented by formula (I), or the salt of the compound represented by formula (I), to obtain the nicotinic acid represented by formula (V):

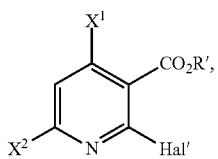

(V)

or the salt of the compound represented by formula (V).

7. The method according to claim 5, comprising:
(i) reacting a compound represented by formula (III):

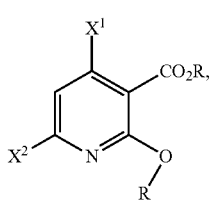

(III)

wherein:
each of $X^1$ and $X^2$ which are independent of each other, is a hydrogen atom, a halogen atom, an alkyl group, an alkoxy group, a haloalkyl group, or a haloalkoxy group;
R' is an alkyl group; and
Hal' is a fluorine atom, a chlorine atom, or a bromine atom, or
a salt of the compound represented by formula (III), with an alkali metal alkoxide represented by formula (IV):

RO-M     (IV), wherein R is an alkyl group, and M is an alkali metal atom, to obtain a compound represented by formula (II):

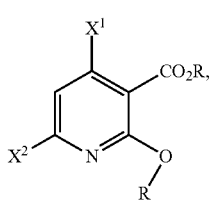

(II)

or the salt of the compound represented by formula (II);
(ii) reacting the compound of formula (II), or the salt thereof, obtained in (i), with the halogenating agent, to obtain the nicotinic acid derivative represented by formula (I):

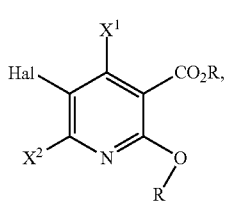

(I)

wherein Hal is a chlorine atom or a bromine atom, or the salt of the compound represented by formula (I); and (iii) hydrolyzing the compound of formula (I), or the salt thereof, obtained in (ii), to obtain a nicotinic acid represented by formula (V):

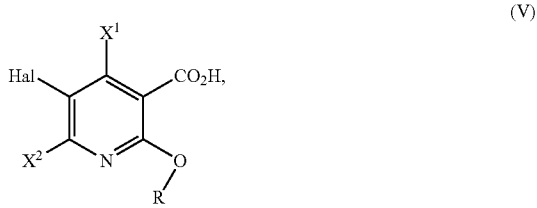
(V)

or a salt of the compound represented by formula (V).

8. The method of claim 1, wherein the salt of the compound of formula (I) is selected from the group consisting of a hydrochloride, a hydrobromide, a phosphate, a sulfate, a nitrate, an acetate, a p-toluenesulfonate, a methanesulfonate, a propanesulfonate, a sodium salt, a potassium salt, a magnesium salt, and a calcium salt.

9. The method of claim 1, wherein the reacting is carried out in a solvent selected from the group consisting of chlorobenzene, dichlorobenzene, hexane, cyclohexane, methylene chloride, 1,2-dichloroethane, tetrahydrofuran, 1,2-dimethoxyethane, acetic acid, methyl acetate, ethyl acetate, acetonitrile, propionitrile, N,N-dimethylformamide, and dimethylsulfoxide.

10. The method of claim 9, wherein the solvent is an ester.

11. The method of claim 1, wherein the halogenating agent is selected from the group consisting of chlorine, bromine, sulfuryl chloride, sodium hypochlorite, N-chlorosuccinimide, N-bromosuccinimide, 1,3-dichloro-5,5-dimethylhydantoin, and 1,3-dibromo-5,5-dimethylhydantoin.

12. The method of claim 1, wherein a base is present in the reacting.

13. The method of claim 12, wherein the base is selected from the group consisting of sodium hydroxide, potassium hydroxide, sodium carbonate, potassium carbonate, sodium acetate, potassium acetate, sodium hydrogencarbonate, potassium hydrogencarbonate, pyridine, triethylamine.

14. The method of claim 12, wherein the base is sodium acetate.

15. The method of claim 1, wherein at least one of $X^1$ and $X^2$ is alkyl.

16. The method of claim 5, wherein at least one of $X^1$ and $X^2$ is alkyl.

* * * * *